(12) United States Patent
Islam et al.

(10) Patent No.: US 11,629,299 B1
(45) Date of Patent: Apr. 18, 2023

(54) PROCESSES FOR PRODUCING PETROCHEMICAL PRODUCTS THAT UTILIZE A RISER AND A DOWNER WITH SHARED CATALYST REGENERATOR

(71) Applicant: Saudi Arabian Oil Company, Dhahran (SA)

(72) Inventors: Md Ashraful Islam, Dhahran (SA); Abdennour Bourane, Dhahran (SA); Juttu Gopal, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/570,526

(22) Filed: Jan. 7, 2022

(51) Int. Cl.
    *C10G 11/18*   (2006.01)
    *C07C 4/06*    (2006.01)
    *C10G 59/02*   (2006.01)

(52) U.S. Cl.
    CPC .............. *C10G 59/02* (2013.01); *C07C 4/06* (2013.01); *C10G 2300/301* (2013.01);
    (Continued)

(58) Field of Classification Search
    CPC .............. C10G 59/02; C10G 2300/301; C10G 2300/4006; C10G 2300/70; C10G 2400/20; C07C 4/06
    See application file for complete search history.

(56) References Cited

U.S. PATENT DOCUMENTS 5,009,769 A    4/1991  Goelzer
5,372,704 A   12/1994  Harandi et al.
(Continued)

FOREIGN PATENT DOCUMENTS

CN   101210191 A   7/2008
CN   109666505 A   4/2019
(Continued)

OTHER PUBLICATIONS

Akah et al., "Maximizing propylene production via FCC technology", Appl Petrochem Res, vol. 5, pp. 377-392, 2015.
Akah et al., "Reactivity of naphtha fractions for light olefins production", Int. J. Ind. Chem. vol. 8, pp. 221-233, 2017.
(Continued)

*Primary Examiner* — In Suk C Bullock
*Assistant Examiner* — Jason Y Chong
(74) *Attorney, Agent, or Firm* — Dinsmore & Shohl LLP

(57) ABSTRACT

Petrochemical products may be produced from a hydrocarbon material by a process that may include separating the hydrocarbon material into at least a lesser boiling point fraction and a greater boiling point fraction, cracking the lesser boiling point fraction in a first reactor in the presence of a catalyst at a reaction temperature of from 500° C. to 700° C. to produce a first cracking reaction product, and cracking the greater boiling point fraction in a second reactor in the presence of the catalyst at a reaction temperature of from 500° C. to 700° C. to produce a second cracking reaction product. The hydrocarbon material may be crude oil. The first reactor may be a riser, and the second reactor may be a downer. The catalyst may be passed from the first reactor to the second reactor, from the second reactor to a regenerator, and from the regenerator to the first reactor, such that the catalyst is circulated between the first reactor, second reactor, and regenerator. An amount of coke may be reduced on the catalyst in the regenerator.

15 Claims, 1 Drawing Sheet

(52) U.S. Cl.
CPC ............. *C10G 2300/4006* (2013.01); *C10G 2300/70* (2013.01); *C10G 2400/20* (2013.01)

(56) References Cited

U.S. PATENT DOCUMENTS

| | | | |
|---|---|---|---|
| 5,730,859 | A | 3/1998 | Johnson et al. |
| 5,904,837 | A | 5/1999 | Fujiyama |
| 5,951,850 | A | 9/1999 | Ino et al. |
| 6,287,522 | B1 | 9/2001 | Lomas |
| 6,656,346 | B2 | 12/2003 | Ino et al. |
| 6,877,042 | B2 | 4/2005 | Tawil et al. |
| 7,491,315 | B2 | 2/2009 | Eng et al. |
| 9,290,705 | B2 | 3/2016 | Bourane et al. |
| 9,434,892 | B2 | 9/2016 | Pradeep et al. |
| 9,458,394 | B2 | 10/2016 | Dean et al. |
| 11,434,437 | B1 | 9/2022 | Zhang et al. |
| 2018/0346827 | A1* | 12/2018 | Al-Ghamdi ............... B01J 8/26 |
| 2021/0284921 | A1 | 9/2021 | Marri et al. |

FOREIGN PATENT DOCUMENTS

| | | |
|---|---|---|
| CN | 113462428 A | 10/2021 |
| WO | 2018222338 A1 | 12/2018 |

OTHER PUBLICATIONS

Corma et al., "Different process schemes for converting light straight run and fluid catalytic cracking naphtahas in a FCC unit for maximum propylene production", Applied Catalysis A: General, vol. 265, pp. 195-206, 2004.

Liu et al., "Study on the FCC Process of a Novel Riser—Downer Coupling REactor (III): Industrial Trial and CFD Modeling", Ind. Eng. Chem. Res., vol. 47, pp. 8582-8587, 2008.

Verstraete et al., "Study of direct and indirect naphtha recycling to a resid FCC unit for maximum propylene production", Catalysis Today, vol. 106, pp. 62-71, 2005.

Notification of Transmittal of the International Search Report and the Written Opinion of the International Searching Authority, or the Declaration dated Jan. 9, 2023 pertaining to International application No. PCT/US2022/043474 filed Sep. 14, 2022, pp. 1-13.

* cited by examiner

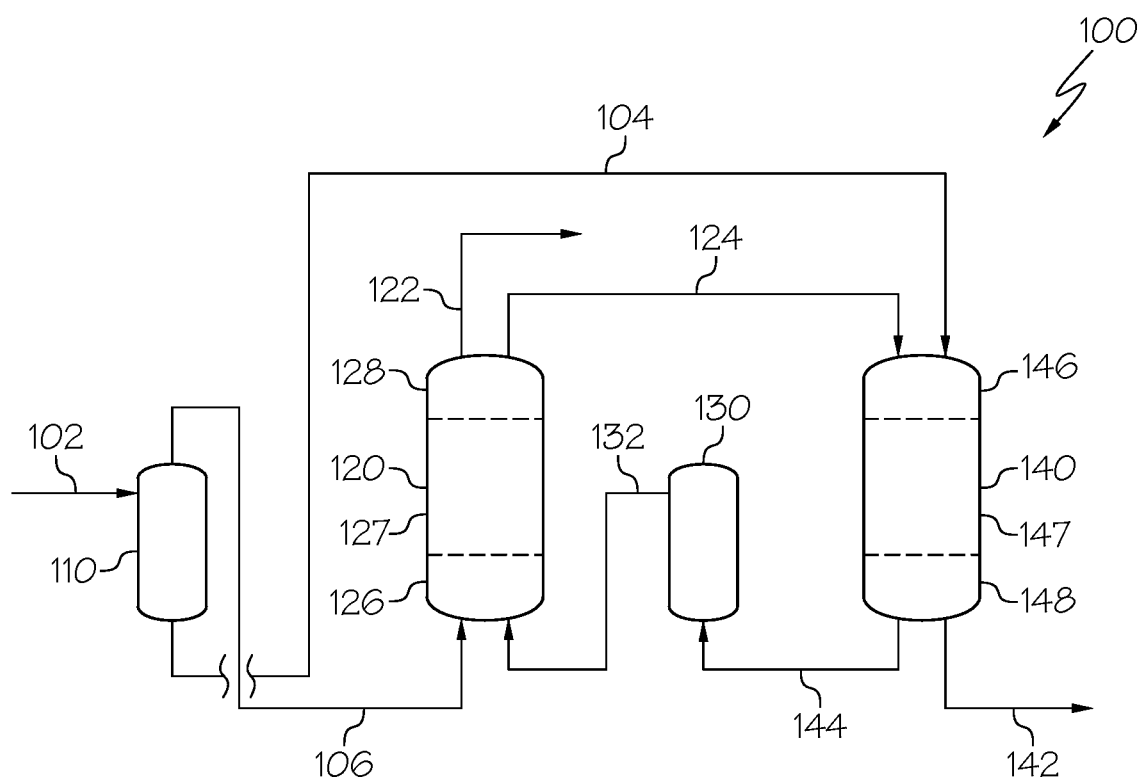

PROCESSES FOR PRODUCING PETROCHEMICAL PRODUCTS THAT UTILIZE A RISER AND A DOWNER WITH SHARED CATALYST REGENERATOR

TECHNICAL FIELD

Embodiments of the present disclosure generally relate to chemical processing and, more specifically, to processes and systems utilizing fluid catalytic cracking to form olefins.

BACKGROUND

Ethylene, propene, butene, butadiene, and aromatics compounds such as benzene, toluene and xylenes are basic intermediates for a large proportion of the petrochemical industry. They are usually obtained through the thermal cracking (or steam pyrolysis) of petroleum gases and distillates such as naphtha, kerosene or even gas oil. These compounds are also produced through refinery fluidized catalytic cracking (FCC) processes where classical heavy feedstocks such as gas oils or residues are converted. Typical FCC feedstocks range from hydrocracked bottoms to heavy feed fractions such as vacuum gas oil and atmospheric residue; however, these feedstocks are limited. The second most important source for propene production is currently refinery propene from FCC reactor units. With the ever-growing demand, FCC reactor unit owners look increasingly to the petrochemicals market to boost their revenues by taking advantage of economic opportunities that arise in the propene market.

The worldwide increasing demand for light olefins remains a major challenge for many integrated refineries. In particular, the production of some valuable light olefins such as ethylene, propene, and butene has attracted increased attention as pure olefin streams are considered the building blocks for polymer synthesis. The production of light olefins depends on several process variables like the feed type, operating conditions, and the type of catalyst.

SUMMARY

Despite the options available for producing a greater yield of propene and other light olefins, intense research activity in this field is still being conducted. These options include the use of high severity fluid catalytic cracking ("HSFCC") systems, developing more selective catalysts for the process, and enhancing the configuration of the process in favor of more advantageous reaction conditions and yields. The HSFCC process is capable of producing yields of propene up to four times greater than the traditional fluid catalytic cracking unit and greater conversion levels for a range of petroleum streams. Embodiments of the present disclosure are directed to improved HSFCC systems and processes for producing one or more petrochemical products from a hydrocarbon material, such as a crude oil.

In the embodiments described herein, two FCC reactors are utilized, where one FCC is a riser and the other FCC is a downer. Crude oil is fractionated into heavy (greater boiling point) and light (lesser boiling point) streams, where the light stream is passed to the riser and the heavy stream is passed to the downer. The two HSFCC reactors utilize the same catalyst, where the catalyst is cycled from a regenerator to the riser, to the downer, and back to the regenerator. Such a configuration may produce desirable yields of light olefins while minimizing catalyst stock needed for the reactions. These embodiments allow, in one or more embodiments, for the lesser boiling point fraction to be cracked at higher temperatures, greater residence time, and with more active catalyst than the greater boiling point fraction, while conserving catalyst loads.

According to one or more embodiments, petrochemical products may be produced from a hydrocarbon material by a process that may comprise separating the hydrocarbon material into at least a lesser boiling point fraction and a greater boiling point fraction, cracking the lesser boiling point fraction in a first reactor in the presence of a catalyst at a reaction temperature of from 500° C. to 700° C. to produce a first cracking reaction product, and cracking the greater boiling point fraction in a second reactor in the presence of the catalyst at a reaction temperature of from 500° C. to 700° C. to produce a second cracking reaction product. The hydrocarbon material may be crude oil. The first reactor may be a riser, and the second reactor may be a downer. The catalyst may be passed from the first reactor to the second reactor, from the second reactor to a regenerator, and from the regenerator to the first reactor, such that the catalyst is circulated between the first reactor, second reactor, and regenerator. An amount of coke may be reduced on the catalyst in the regenerator.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 1 is a generalized schematic diagram of a hydrocarbon feed conversion system, according to one or more embodiments described in this disclosure.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrocracking units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Further-more, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in one or more embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in some embodiments, less than all of the streams signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to systems and processes for converting one or more hydrocarbon feed streams into one or more petrochemical products using a high-severity fluidized catalytic cracking (HSFCC) system that includes a riser and a downer, where each unit is operated at high-severity conditions. For example, a method for operating a system having a first FCC reactor unit and a second FCC reactor unit may include separating the hydrocarbon feed stream into a lesser boiling point fraction and a greater boiling point fraction in the feed separator. As is described herein, catalyst is cycled through both the riser and the downer, which share a regenerator. These embodiments allow for the lesser boiling point fraction to be cracked at higher temperatures, greater residence time, and with more active catalyst than the greater boiling point fraction, while conserving catalyst loads.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As described herein, a "riser" is a type of reactor where the general movement of the feed through the reactor is upwards. A riser generally also has an upward catalyst flow, such that the feed and catalyst are co-current. A "downer" is a type of reactor where the general movement of the feed through the reactor is downwards. A downer generally also has a downward catalyst flow, such that the feed and catalyst are co-current.

As used in this disclosure, a "separation unit" refers to any separation device or system of separation devices that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "lesser boiling point fraction" (sometimes referred to as a "light fraction") and a "greater boiling point fraction" (sometimes referred to as a "heavy fraction") may exit the separation unit, where, on average, the contents of the lesser boiling point fraction stream have a lesser boiling point than the greater boiling point fraction stream. Other streams may fall between the lesser boiling point fraction and the greater boiling point fraction, such as an "intermediate boiling point fraction."

As used in this disclosure, the term "high-severity conditions" generally refers to FCC temperatures of 500° C. or greater, and a weight ratio of catalyst to hydrocarbon (catalyst to oil ratio) of equal to or greater than 5:1, all of which may be more severe than typical FCC reaction conditions.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used in this disclosure, a "catalyst" refers to any substance that increases the rate of a specific chemical reaction. Catalysts described in this disclosure may be utilized to promote various reactions, such as, but not limited to, cracking (including aromatic cracking). As used in this disclosure, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a alkyl or cyclic moiety, such as a alkane, cycloalkane, naphthalene, an aromatic or the like, to an olefinic compound and/or a compound which does not include a cyclic moiety or contains fewer cyclic moieties than prior to cracking.

As used in this disclosure, the term "spent catalyst" refers to catalyst that has been introduced to and passed through a cracking reaction zone to crack a hydrocarbon material, such as the greater boiling point fraction or the lesser boiling point fraction, for example, but has not been regenerated in the regenerator. Semi-spent catalyst refers to catalyst that is not completely spent. Generally, spent catalyst highly reduced activity due to, for example coke deposited on the catalyst. Semi-spent catalyst may have somewhat reduced activity, but not as reduced as the spent catalyst. The "spent catalyst" may have coke deposited on the catalyst and may include partially coked catalyst as well as fully coked catalysts. The amount of coke deposited on the "spent catalyst" may be greater than the amount of coke remaining on the regenerated catalyst following regeneration.

As used in this disclosure, the term "regenerated catalyst" refers to catalyst that has been introduced to a cracking reaction zone and then regenerated in a regenerator to heat the catalyst to a greater temperature, oxidize and remove at least a portion of the coke from the catalyst to restore at least a portion of the catalytic activity of the catalyst, or both. The "regenerated catalyst" may have less coke, a greater temperature, or both compared to spent catalyst and may have greater catalytic activity compared to spent catalyst. The "regenerated catalyst" may have more coke and lesser catalytic activity compared to fresh catalyst that has not passed through a cracking reaction zone and regenerator.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "propylene stream" passing from a first system component to a second system component should be understood to equivalently disclose "propylene" passing from a first system component to a second system component, and the like.

Referring now to FIG. 1, a hydrocarbon feed conversion system 100 is schematically depicted. The hydrocarbon feed conversion system 100 may include a feed separator 110, a first FCC reactor unit 120, a second FCC reactor unit 140, and a regenerator 130. The hydrocarbon feed conversion system 100 generally receives a hydrocarbon feed stream 102 and directly processes the hydrocarbon feed stream 102 to produce system product streams 122, 142.

In general terms, the hydrocarbon feed conversion system 100 includes two FCC reactor units in each of which a portion of the hydrocarbon feed stream 102 contacts heated fluidized catalytic particles in a cracking reaction zone maintained at high-severity temperatures and pressures. When the portion of the hydrocarbon feed stream 102 contacts the hot catalyst and is cracked to lighter products, carbonaceous deposits, commonly referred to as coke, form on the catalyst. The coke deposits formed on the catalyst may reduce the catalytic activity of the catalyst or deactivate the catalyst. Deactivation of the catalyst may result in the catalyst becoming catalytically ineffective. The spent catalyst having coke deposits may be separated from the cracking reaction products, stripped of removable hydrocarbons, and passed to a regeneration process where the coke is burned from the catalyst in the presence of air to produce a regenerated catalyst that is catalytically effective. The term "catalytically effective" refers to the ability of the regenerated catalyst to increase the rate of cracking reactions. The term "catalytic activity" refers to the degree to which the regenerated catalyst increases the rate of the cracking reactions and may be related to a number of catalytically active sites available on the catalyst. For example, coke deposits on the catalyst may cover up or block catalytically active sites on the spent catalyst, thus, reducing the number of catalytically active sites available, which may reduce the catalytic activity of the catalyst. Following regeneration, the regenerated catalyst may have equal to or less than 10 wt. %, 5 wt. %, or even 1 wt. % coke based on the total weight of the regenerated catalyst. The combustion products may be removed from the regeneration process as a flue gas stream. The heated regenerated catalysts may then be recycled back to the cracking reaction zone of the FCC reactor units.

The hydrocarbon feed stream 102 may generally comprise a hydrocarbon material. In embodiments, the hydrocarbon material of the hydrocarbon feed stream 102 may be crude oil. As used in this disclosure, the term "crude oil" is to be understood to mean a mixture of petroleum liquids, gases, solids, or combinations of these, including in some embodiments impurities such as sulfur-containing compounds, nitrogen-containing compounds and metal compounds that has not undergone significant separation or reaction processes. Crude oils are distinguished from fractions of crude oil. In certain embodiments the crude oil feedstock may be a minimally treated light crude oil to provide a crude oil feedstock having total metals (Ni+V) content of less than 10 parts per million by weight (ppmw) and Conradson carbon residue of less than 5 wt %. For example, minimal treatment may include hydroprocessing to remove, for example, heavy metals.

In one or more embodiments, the hydrocarbon feed stream 102 is crude oil, which may have an American Petroleum Institute (API) gravity of from 22 degrees to 40 degrees. For example, the hydrocarbon feed stream 102 utilized may be an Arab heavy crude oil (API gravity of approximately 28°), Arab medium (API gravity of approximately 30°), Arab light (API gravity of approximately 33°), or Arab extra light (API gravity of approximately 39°).

In general, the contents of the hydrocarbon feed stream 102 may include a relatively wide variety of chemical species based on boiling point, characteristic of unprocessed crude oils that have not been separated into fractions. For example, the hydrocarbon feed stream 102 may have composition such that the difference between the 5 wt. % boiling point and the 95 wt. % boiling point of the hydrocarbon feed stream 102 is at least 100° C., at least 200° C., at least 300° C., at least 400° C., at least 500° C., or even at least 600° C.

The hydrocarbon feed stream 102 may be introduced to the feed separator 110 which may separate the contents of the hydrocarbon feed stream 102 into at least a lesser boiling point fraction stream 106 and a greater boiling point fraction stream 104. In one or more embodiments, at least 90 wt. %, at least 95 wt. %, at least 99 wt. %, or even at least 99.9 wt. % of the hydrocarbon feed stream may be present in the combination of the lesser boiling point fraction stream 106 and a greater boiling point fraction stream 104. In one or more embodiments, the feed separator 110 may be a vapor-liquid separator such as a flash drum (sometimes referred to as a breakpot, knock-out drum, knock-out pot, compressor suction drum, or compressor inlet drum). In embodiments that utilize a vapor-liquid separator as the feed separator 110, the greater boiling point fraction stream 104 may exit the feed separator 110 as a liquid and the lesser boiling point fraction stream 106 may exit the feed separator 110 as a vapor. The vapor-liquid separator may be operated at a temperature and pressure suitable to separate the hydrocarbon feed stream 102 into the lesser boiling point fraction stream 106 and the greater boiling point fraction stream 104. The cut temperature or "cut point" (that is, the approximate atmospheric boiling point temperature separating the lesser boiling point fraction stream 106 and the greater boiling point fraction stream 104) of the vapor-liquid separator may be from 250° C. to 400° C. As such, all components of the lesser boiling point fraction stream may have a boiling point (at atmospheric pressure) of less than or equal to 400° C., less than or equal to 375° C., less than or equal to 350° C., less than or equal to 325° C., less than or equal to 300° C., or less than or equal to 250° C., and all components of the greater boiling point fraction stream may have a boiling point (at atmospheric pressure) of at least 250° C., at least 300° C., at least 325° C., at least 350° C., at least 375° C., or at least 400° C.

In one or more embodiments, the cut point may be approximately 350° C., such as in a range of from 340° C. to 360° C., or from 345° C. to 355° C. In such embodiments, if Arab extra light crude is utilized as a feedstock, the 350° C.+fraction may include 98.7 wt. % slurry oil, 0.8 wt. % light cycle oil, and 0.5 wt. % naphtha. In such embodiments, the 350° C.− fraction may include 57.5 wt. % naphtha, 38.9 wt. % light cycle oil, and 3.7 wt. % slurry oil.

One or more supplemental feed streams (not shown) may be added to the hydrocarbon feed stream 102 prior to introducing the hydrocarbon feed stream 102 to the feed separator 110. As previously described, in one or more embodiments, the hydrocarbon feed stream 102 may be crude oil. In one or more embodiments, the hydrocarbon feed stream 102 may be crude oil, and one or more supplemental feed streams comprising one or more of a vacuum residue, tar sands, bitumen, atmospheric residue, vacuum gas oils, demetalized oils, naphtha streams, other hydrocarbon streams, or combinations of these materials, may be added to the crude oil upstream of the feed separator 110.

Still referring to FIG. 1, the lesser boiling point fraction stream 106 may be passed to a first FCC reactor unit 120, where it is catalytically cracked. The first FCC reactor unit 120 may be a riser, where catalyst and reactant move in an upward direction during reaction. The first FCC reactor unit 120 may include a mixing zone 126, a first cracking reaction zone 127, and a catalyst separation zone 128. The lesser boiling point fraction stream 106 may be added to the mixing zone 126 along with the catalyst passed from the regenerator 130 in catalyst stream 132. The lesser boiling point fraction stream 106 may be combined or mixed with the catalyst from catalyst stream 132 and cracked in the first cracking reaction zone 127 to produce a mixture of a semi-spent catalyst and a first cracking reaction product, which are separated in catalyst separation zone 128. The first cracking reaction product may be passed out of the first reactor 120 in first cracking reaction product stream 122. The separated semi-spent catalyst is passed out of the first reactor 120 in semi-spent catalyst stream 124.

Still referring to FIG. 1, the greater boiling point fraction stream 104 may be passed to a second FCC reactor unit 140, where it is catalytically cracked. The second FCC reactor unit 140 may be a downer, where catalyst and reactant move in a downward direction during reaction. The second FCC reactor unit 140 may include a mixing zone 146, a second cracking reaction zone 147, and a catalyst separation zone 148. The greater boiling point fraction stream 104 may be added to the mixing zone 146 along with the catalyst passed from the first FCC reactor unit 120 in catalyst stream 124. The greater boiling point fraction stream 104 may be combined or mixed with the catalyst from catalyst stream 124 and cracked in the second cracking reaction zone 147 to produce a mixture of a spent catalyst and a second cracking reaction product, which are separated in catalyst separation zone 148. The first cracking reaction product may be passed out of the second reactor 140 in second cracking reaction product stream 142. The separated spent catalyst is passed out of the second reactor 140 in spent catalyst stream 144.

According to one or more embodiments, the first FCC reactor unit 120 and the second FCC reactor unit 140 may operate at temperatures of from 500° C. to 700° C. For example, the first FCC reactor unit 120 and the second FCC reactor unit 140 may operate at temperatures of from 500° C. to 525° C., from 525° C. to 550° C., from 550° C. to 575° C., from 575° C. to 600° C., from 600° C. to 625° C., from 625° C. to 650° C., from 650° C. to 675° C., from 675° C. to 700° C., or any combination of these ranges.

According to some embodiments, the first FCC reactor unit 120 may operate at a greater temperature than the second FCC reactor unit 140. For example, the first FCC reactor unit 120 may operate at a temperature of from 600° C. to 680° C., and the second FCC reactor unit 140 may operate at a temperature of from 580° C. to 650° C. For example, the first FCC reactor unit 120 may operate at a temperature of from 600° C. to 620° C., from 620° C. to 640° C., from 640° C. to 660° C., from 660° C. to 680° C., or any combinations of these ranges. For example, the second FCC reactor unit 140 may operate at a temperature of from 580° C. to 600° C., from 600° C. to 620° C., from 620° C. to 640° C., from 640° C. to 650° C., or combinations of these ranges. In embodiments, the first FCC reactor unit 120 may operate at a temperature at least 5° C. greater, at least 10° C. greater, at least 15° C. greater, at least 20° C. greater, at least 25° C. greater, at least 30° C. greater, at least 35° C. greater, at least 40° C. greater, at least 45° C. greater, or even at least 50° C. greater than the second FCC reactor unit 140.

According to embodiments, the catalyst to hydrocarbon ratio in the first FCC reactor unit 120 and the second FCC reactor unit 140 may be from 10:1 to 40:1. For example, the catalyst to hydrocarbon ratio in the first FCC reactor unit 120 may be from 10:1 to 15:1, from 15:1 to 20:1, from 20:1 to 25:1, from 25:1 to 30:1, or combinations of these ranges. The catalyst to hydrocarbon ratio in the second FCC reactor unit 140 may be from 10:1 to 15:1, from 15:1 to 20:1, from 20:1 to 25:1, from 25:1 to 30:1, from 30:1 to 35:1, from 35:1 to 40:1, or combinations of these ranges.

In one or more embodiments, the residence time in the first FCC reactor unit 120 (i.e., the average time of catalyst and hydrocarbon contact) may be greater than the residence time in the second FCC reactor unit 140, such as by at least 0.1 seconds (sec), at least 0.2 sec, at least 0.3 sec, at least 0.4 sec, at least 0.5 sec, at least 0.6 sec, at least 0.7 sec, at least 0.8 sec, at least 0.9 sec, at least 1 sec, at least 2 sec, or even at least 3 sec. Generally, risers may have longer residence times than downers when somewhat similar in size, so that the use of a riser as the first FCC reactor unit 120 and a downer as the second FCC reactor unit 140 accounts majorly for the difference in residence time between the first FCC reactor unit 120 and the second FCC reactor unit 140. In embodiments, the residence time of the first FCC reactor unit may be from 0.2 to 5 sec, from 0.5 sec to 1 sec, from 1 sec to 1.5 sec, from 1.5 sec to 2 sec, from 2 sec to 2.5 sec, from 2.5 sec to 3 sec, or from 3 sec to 3.5 sec, from 3.5 sec to 4 sec, from 4 sec to 4.5 sec, from 4.5 sec to 5 sec, or combinations of these ranges. In embodiments, the residence time of the second FCC reactor unit may be from 0.2 seconds (sec) to 5 sec, from 0.5 sec to 1 sec, from 1 sec to 1.5 sec, from 1.5 sec to 2 sec, from 2 sec to 2.5 sec, from 2.5 sec to 3 sec, or from 3 sec to 3.5 sec, from 3.5 sec to 4 sec, from 4 sec to 4.5 sec, from 4.5 sec to 5 sec, or combinations of these ranges.

The first cracking reaction product stream 122 and the second cracking reaction product stream 142 each may include a mixture of cracked hydrocarbon materials, which may be further separated into one or more greater value petrochemical products and recovered from the system. For example, the first cracking reaction product stream 122, the second cracking reaction product stream 142, or both, may include one or more of cracked gas oil, cracked gasoline, cracked naphtha, mixed butenes, butadiene, propene, ethylene, other olefins, ethane, methane, other petrochemical products, or combinations of these. The cracked gasoline may be further processed to obtain aromatics such as benzene, toluene, xylenes, or other aromatics for example.

Still referring to FIG. 1, the catalyst in the hydrocarbon feed conversion system 100 may be recycled by passing from the first FCC reactor unit 120 to the second FCC reactor unit 140 to the regenerator 130 and back to the first FCC reactor unit 120 in a continuous loop via catalyst streams 124, 144, and 132. As such, the same catalyst is utilized in the reactions in the first FCC reactor unit 120 and the second FCC reactor unit 140.

In embodiments, the regenerator 130 processes the catalyst by removing coke (i.e., at least a major portion of the coke) and raising the catalyst temperature (by the burning of coke for example). As described herein, the "removing" of coke from the catalyst refers to removal of at least a portion of the coke, but some residual coke may remain on the catalyst, as would be understood by those skilled in the art. The catalyst passed from the regenerator 130 to the first FCC reactor unit 120 is regenerated catalyst, and has relatively high catalytic activity. The catalyst passed from the first FCC reactor unit 120 to the second FCC reactor unit 140 is semi-spent catalyst, and has moderate catalytic activity. The catalyst passed from the second FCC reactor unit 140 to the regenerator 130 is spent catalyst, and has relatively low catalytic activity.

The catalyst used in the hydrocarbon feed conversion system 100 may include one or more fluid catalytic cracking catalysts that are suitable for use in the first FCC reactor unit 120 and the second FCC reactor unit 140. The catalyst may be a heat carrier and may provide heat transfer to the first FCC reactor unit 120 and the second FCC reactor unit 140. The catalyst may also have a plurality of catalytically active sites, such as acidic sites for example, that promote the cracking reaction. For example, in embodiments, the catalyst may be a high-activity FCC catalyst having high catalytic activity. Examples of fluid catalytic cracking catalysts suitable for use in the hydrocarbon feed conversion system 100 may include, without limitation, zeolites, silica-alumina catalysts, carbon monoxide burning promoter additives, bottoms cracking additives, light olefin-producing additives, other catalyst additives, or combinations of these components. Zeolites that may be used as at least a portion of the catalyst for cracking may include, but are not limited to Y, REY, USY, RE-USY zeolites, or combinations of these. The catalyst may also include a shaped selective catalyst additive, such as ZSM-5 zeolite crystals or other pentasil-type catalyst structures, which are often used in other FCC processes to produce light olefins and/or increase FCC gasoline octane. In one or more embodiments, the catalyst may include a mixture of a ZSM-5 zeolite crystals and the cracking catalyst zeolite and matrix structure of a typical FCC cracking catalyst. In one or more embodiments, the catalyst may be a mixture of Y and ZSM-5 zeolite catalysts embedded with clay, alumina, and binder.

In one or more embodiments, at least a portion of the catalyst may be modified to include one or more rare earth elements (15 elements of the Lanthanide series of the IUPAC Periodic Table plus scandium and yttrium), alkaline earth metals (Group 2 of the IUPAC Periodic Table), transition metals, phosphorus, fluorine, or any combination of these, which may enhance olefin yield in the first cracking reaction zone 122, second cracking reaction zone 142, or both. Transition metals may include "an element whose atom has a partially filled d sub-shell, or which can give rise to cations with an incomplete d sub-shell" [IUPAC, Compendium of Chemical Terminology, 2nd ed. (the "Gold Book") (1997). Online corrected version: (2006—) "transition element"]. One or more transition metals or metal oxides may also be impregnated onto the catalyst. Metals or metal oxides may include one or more metals from Groups 6-10 of the IUPAC Periodic Table. In some embodiments, the metals or metal oxides may include one or more of molybdenum, rhenium, tungsten, or any combination of these. In one or more embodiments, a portion of the catalyst may be impregnated with tungsten oxide.

The regenerator 130 may by any suitable combustion regenerator, where combustion gas such as air or other oxygen containing gas streams are passed into the regenerator 130 and flue gas is expelled. The combustion gases may include one or more of combustion air, oxygen, fuel gas, fuel oil, other components, or any combinations of these. In the regenerator 130, the coke deposited on the spent catalyst from the second FCC reactor unit 140 may at least partially oxidize (combust) in the presence of the combustion gases to form at least carbon dioxide and water. In some embodiments, the coke deposits on the spent catalyst may be fully oxidized in the regenerator 130. Other organic compounds, such as residual first cracking reaction product or second cracking reaction product for example, may also oxidize in the presence of the combustion gases in the regenerator 130. Other gases, such as carbon monoxide for example, may be formed during coke oxidation in the regenerator 130. Oxidation of the coke deposits produces heat, which may be transferred to and retained by the regenerated catalyst passed to the first FCC reactor unit 120 via catalyst stream 132.

Generally, the regenerated catalyst has less coke deposit than the semi-spent catalyst, and the semi-spent catalyst has less coke deposit than the spent catalyst. The regenerated catalyst passing out of the regenerator 130 may have less than 1 wt. % coke deposits, based on the total weight of the regenerated catalyst. In some embodiments, the regenerated catalyst passing out of the regenerator 130 may have less than 0.5 wt. %, less than 0.1 wt. %, or less than 0.05 wt. % coke deposits. In some embodiments, the regenerated catalyst passing out of the regenerator 130 to the first FCC reactor unit 120 may have from 0.001 wt. % to 1 wt. %, from 0.001 wt. % to 0.5 wt. %, from 0.001 wt. % to 0.1 wt. %, from 0.001 wt. % to 0.05 wt. %, from 0.005 wt. % to 1 wt. %, from 0.005 wt. % to 0.5 wt. %, from 0.005 wt. % to 0.1 wt. %, from 0.005 wt. % to 0.05 wt. %, from 0.01 wt. % to 1 wt. %, from 0.01 wt. % to 0.5 wt. % to 0.01 wt. % to 0.1 wt. %, from 0.01 wt. % to 0.05 wt. % coke deposits, based on the total weight of the regenerated catalyst. In one or more embodiments, the regenerated catalyst passing out of regenerator 130 may be substantially free of coke deposits. As used in this disclosure, the term "substantially free" of a component means less than 1 wt. % of that component in a particular portion of a catalyst, stream, or reaction zone. As an example, the regenerated catalyst that is substantially free of coke deposits may have less than 1 wt. % of coke deposits. Removal of the coke deposits from the regenerated catalyst in the regenerator 130 may remove the coke deposits from the catalytically active sites, such as acidic sites for example, of the catalyst that promote the cracking reaction. Removal of the coke deposits from the catalytically active sites on the catalyst may increase the catalytic activity of the regenerated catalyst compared to the spent catalyst passing from the second FCC reactor unit 140. Thus, the regenerated catalyst may have a catalytic activity that is greater than the spent catalyst passed from the second FCC reactor unit 140 and the semi-spent catalyst passed from the first FCC reactor unit 120 to the second FCC reactor unit 140.

The regenerated catalyst may absorb at least a portion of the heat generated from combustion of the coke deposits. The heat may increase the temperature of the regenerated catalyst compared to the temperature of the spent catalyst.

The methods described herein have numerous advantages over conventional FCC systems. For example, when the hydrocarbon feed stream 102 is cut such that a greater boiling point fraction stream 104 and lesser boiling point fraction stream 106 are formed, the presently disclosed processes allow for enhanced conversion by treating the greater boiling point fraction stream 104 and lesser boiling point fraction stream 106 with different reaction conditions by utilizing a riser as the first FCC reactor unit 120 and a downer as the second FCC reactor unit 140, and by cycling the catalyst as described. Without being bound by theory, it is believed that the greater boiling point fraction stream 104 may be cracked with lower temperatures, lower residence time, and with less active catalyst than the lesser boiling point fraction stream 106. The systems described herein achieve this result by utilizing a riser and downer in the first FCC reactor unit 120 and second FCC reactor unit 140, respectively, to control residence time. Also, by cycling the catalyst as described, large loads of heat may be passed to the first FCC reactor unit 120 by the combustion of the catalyst in the regenerator 130 immediately upstream. Lower temperatures in the second FCC reactor unit 140 are tolerated, allowing for the catalyst to be passed from the first FCC reactor unit 120 to the second FCC reactor unit 140 without an intermediate regeneration step. Additionally, the catalytic activity used to treat the greater boiling point fraction stream 104 in the second FCC reactor unit 140 may be relatively low, allowing for the non-necessity of a catalyst regeneration step immediately upstream of the second FCC reactor unit 140.

Moreover, it has been found that the cracking of the lesser boiling point fraction stream 106 in the first FCC reactor unit 120 does not form great amounts of coke, so the catalytic activity in the second FCC reactor unit 140 is tolerable for cracking the heavier materials in the greater boiling point fraction stream 104. Without being bound by theory, it is believed that this reduced coking is due to the lesser ease of cracking of the lesser boiling point fraction stream 106. However, the relatively easier cracking of the greater boiling point fraction stream 104 may cause increased coking, which is immediately mitigated by the direct passing of the catalyst from the second FCC reactor unit 140 to the regenerator 130. Conventional systems may regenerate all catalyst entering an FCC and not loop the catalyst through the first FCC reactor unit 120, second FCC reactor unit 140, and regenerator 130. These and other advantages are presented by the currently disclosed embodiments, as is described herein.

EXAMPLES

The various embodiments of methods and systems for the conversion of feedstock fuels will be further clarified by the following examples. The examples are illustrative in nature, and should not be understood to limit the subject matter of the present disclosure.

Example A

A catalyst was steam treated (100% steam at 810° C. for 6 hours) prior to testing. The steam-treated catalyst was reacted with the lesser boiling point fraction stream (350° C.– of Arab extra light crude at a reactor temperature of 640° C. and a Cat/Oil ratio of 30 wt/wt. The catalyst exiting the reactor ("semi-spent catalyst") was collected in the stripper. This semi-spent catalyst was maintained under an inert (nitrogen) atmosphere and the deposited coke was not burned off. Multiple repeat runs were conducted to collect sufficient amount of catalyst in order to be used for subsequent testing. The carbon remaining on the semi-spent catalyst was measured using a small amount of sample (0.04 wt. % carbon on catalyst). This catalyst was then transferred under inert conditions back into the catalyst feed hopper and then used to react with the greater boiling point fraction stream of Arab extra light crude (350° C.+, marked HF-AXL in Table 1). The testing conditions with the corresponding yields are shown in the second column of Table 1, marked Semi-Spent LF catalyt. These yields are representative of the HF-AXL yield when running the systems presently disclosed, where catalyst to the reactor treating the heavy fraction is first used to crack the lighter fraction. As a comparison, the third column of Table 1 shows the yields when the HF-AXL crude is cracked using fresh steam-treated catalyst, where less coke is present. As is shown, yields of products are comparable, showing that catalyst previously used in the cracking of the light fraction is, unexpectedly, sufficient for cracking the heavy fraction.

TABLE 1

| Feed Catalyst | HF AXL Semi-spent LF catalyst | HF AXL Fresh Catalyst |
|---|---|---|
| Carbon on cat (wt %) | 0.04 | 0.02 |
| Reaction Temp. (° C.) | 608 | 610 |
| Cat/Oil (wt/wt) | 29 | 30 |
| Yield, wt % | | |
| Dry gas & LPG | 46.53 | 46.82 |
| Liquid products | 53.47 | 53.18 |

Multiple aspects of the present application are disclosed herein. In one aspect, a process for producing petrochemical products from a hydrocarbon material may comprise separating the hydrocarbon material into at least a lesser boiling point fraction and a greater boiling point fraction, wherein the hydrocarbon material is crude oil; cracking the lesser boiling point fraction in a first reactor in the presence of a catalyst at a reaction temperature of from 500° C. to 700° C. to produce a first cracking reaction product, wherein the first reactor is a riser; cracking the greater boiling point fraction in a second reactor in the presence of the catalyst at a reaction temperature of from 500° C. to 700° C. to produce a second cracking reaction product, wherein the second reactor is a downer; and passing the catalyst from the first reactor to the second reactor, from the second reactor to a regenerator, and from the regenerator to the first reactor, such that the catalyst is circulated between the first reactor, second reactor, and regenerator, and wherein an amount of coke is reduced on the catalyst in the regenerator.

Another aspect includes any previous aspect, wherein the reaction temperature in the first reactor is greater than the reaction temperature in the second reactor.

Another aspect includes any previous aspect, wherein the reaction temperature in the first reactor is from 600° C. to 680° C.

Another aspect includes any previous aspect, wherein the reaction temperature in the second reactor is from 580° C. to 650° C.

Another aspect includes any previous aspect, wherein the residence in the first reactor is greater than the residence in the second reactor.

Another aspect includes any previous aspect, wherein the residence in the first reactor is from 0.2 seconds to 5 seconds.

Another aspect includes any previous aspect,

Another aspect includes any previous aspect, wherein the residence in the second reactor is from 0.2 second to 2 seconds.

Another aspect includes any previous aspect, wherein the catalyst to hydrocarbon ratio in the first reactor and second reactor is from 10:1 to 40:1.

Another aspect includes any previous aspect, wherein the catalyst passed from the regenerator to the first reactor has greater catalytic activity than the catalyst passed from the first reactor to the second reactor, and the catalyst passed from the first reactor to the second reactor has greater catalytic activity than the catalyst passed from the second reactor to the regenerator.

Another aspect includes any previous aspect, wherein a cut point of the lesser boiling point fraction and the greater boiling point fraction is from 250° C. to 400° C.

Another aspect includes any previous aspect, wherein a cut point of the lesser boiling point fraction and the greater boiling point fraction is from 340° C. to 360° C.

Another aspect includes any previous aspect, wherein the hydrocarbon material has an API gravity of from 22 degrees to 40 degrees.

Another aspect includes any previous aspect, wherein the difference between the 5 wt. % boiling point and the 95 wt. % boiling point of the hydrocarbon material is at least 100° C.

Another aspect includes any previous aspect, wherein at least 90 wt. % of the hydrocarbon material is present in the combination of the greater boiling point fraction and the lesser boiling point fraction.

Another aspect includes any previous aspect, wherein the first cracking reaction product, the second cracking reaction product, or both, comprise at least one of ethylene, propene, butene, or pentene.

For the purposes of defining the present technology, the transitional phrase "consisting of" may be introduced in the claims as a closed preamble term limiting the scope of the claims to the recited components or steps and any naturally occurring impurities.

For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter.

The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B and C should be interpreted as also disclosing a composition "consisting of" components A, B, and C as well as a composition "consisting essentially of" components A, B, and C.

Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

What is claimed is:

1. A process for producing petrochemical products from a hydrocarbon material, the process comprising:
   - separating a crude oil into at least a lesser boiling point fraction and a greater boiling point fraction;
   - cracking the lesser boiling point fraction in a riser reactor in the presence of a catalyst at a reaction temperature of from 500° C. to 700° C. to produce a first cracking reaction product and a semi-spent catalyst;
   - passing the semi-spent catalyst from the riser reactor to a downer reactor;
   - cracking the greater boiling point fraction in the downer reactor in the presence of the semi-spent catalyst at a reaction temperature of from 500° C. to 700° C. to produce a second cracking reaction product and a spent catalyst;
   - passing the spent catalyst from the downer reactor to a regenerator to produce a regenerated catalyst comprising a reduced amount of coke relative to the spent catalyst; and
   - passing the regenerated catalyst from the regenerator to the riser reactor.

2. The process of claim 1, wherein the reaction temperature in the riser reactor is greater than the reaction temperature in the downer reactor.

3. The process of claim 1, wherein the reaction temperature in the riser reactor is from 600° C. to 680° C.

4. The process of claim 1, wherein the reaction temperature in the downer reactor is from 580° C. to 650° C.

5. The process of claim 1, wherein a residence in the riser reactor is greater than a residence in the downer reactor.

6. The process of claim 1, wherein a residence in the riser reactor is from 0.2 seconds to 5 seconds.

7. The process of claim 1, wherein a residence in the downer reactor is from 0.2 second to 2 seconds.

8. The process of claim 1, wherein a catalyst to hydrocarbon ratio in the riser reactor and downer reactor is from 10:1 to 40:1.

9. The process of claim 1, wherein the regenerated catalyst passed from the regenerator to the riser reactor has greater catalytic activity than the semi-spent catalyst passed from the riser reactor to the downer reactor, and the semi-spent catalyst passed from the riser reactor to the downer reactor has greater catalytic activity than the spent catalyst passed from the downer reactor to the regenerator.

10. The process of claim 1, wherein a cut point of the lesser boiling point fraction and the greater boiling point fraction is from 250° C. to 400° C.

11. The process of claim 1, wherein a cut point of the lesser boiling point fraction and the greater boiling point fraction is from 340° C. to 360° C.

12. The process of claim 1, wherein the crude oil has an API gravity of from 22 degrees to 40 degrees.

13. The process of claim 1, wherein a difference between a 5 wt. % boiling point and a 95 wt. % boiling point of the crude oil is at least 100° C.

14. The process of claim 1, wherein at least 90 wt. % of the crude oil is present in a combination of the greater boiling point fraction and the lesser boiling point fraction.

15. The process of claim 1, wherein the first cracking reaction product, the second cracking reaction product, or both, comprise at least one of ethylene, propene, butene, or pentene.

* * * * *